(12) United States Patent
Yoo et al.

(10) Patent No.: US 9,605,135 B2
(45) Date of Patent: Mar. 28, 2017

(54) POLYMER COMPOSITE USING SHEAR THICKENING FLUID

(71) Applicant: KOREA INSTITUTE OF INDUSTRIAL TECHNOLOGY, Cheonan-si, Chungcheongnam-do (KR)

(72) Inventors: Eui Sang Yoo, Jeonju-si (KR); Ju Hea Kim, Seoul (KR); Won Young Jeong, Gunpo-si (KR); Hyun Kyung Lee, Suwon-si (KR); Jae Kyoung Lee, Guri-si (KR); Joon Taek Jun, Ansan-si (KR); Nam Hee Kwon, Seoul (KR); Mi Yeon Kwon, Anyang-si (KR); Dae Young Lim, Yongin-si (KR)

(73) Assignee: KOREA INSTITUTE OF INDUSTRIAL TECHNOLOGY, Cheonan-si, Chungcheongnam-do (KR)

( * ) Notice: Subject to any disclaimer, the term of this patent is extended or adjusted under 35 U.S.C. 154(b) by 0 days.

(21) Appl. No.: 15/035,236

(22) PCT Filed: Dec. 16, 2013

(86) PCT No.: PCT/KR2013/011629
§ 371 (c)(1),
(2) Date: May 9, 2016

(87) PCT Pub. No.: WO2015/068895
PCT Pub. Date: May 14, 2015

(65) Prior Publication Data
US 2016/0289427 A1    Oct. 6, 2016

(30) Foreign Application Priority Data
Nov. 8, 2013 (KR) .................. 10-2013-0135360

(51) Int. Cl.
| | | |
|---|---|---|
| *C08K 9/10* | (2006.01) |
| *A01N 25/28* | (2006.01) |
| *B41M 5/165* | (2006.01) |
| *A61K 9/16* | (2006.01) |
| *B01J 13/22* | (2006.01) |
| *B01J 13/02* | (2006.01) |
| *B01J 13/10* | (2006.01) |
| *B01J 13/20* | (2006.01) |
| *B01J 13/04* | (2006.01) |

(52) U.S. Cl.
CPC ............... *C08K 9/10* (2013.01); *A01N 25/28* (2013.01); *A61K 9/1694* (2013.01); *B01J 13/22* (2013.01); *B41M 5/165* (2013.01); *B01J 13/02* (2013.01); *B01J 13/04* (2013.01); *B01J 13/10* (2013.01); *B01J 13/20* (2013.01)

(58) Field of Classification Search
CPC ......... A01N 25/28; C08K 9/10; B41M 5/165; A61K 9/1694; B01J 13/02; B01J 13/04; B01J 13/10; B01J 13/20
See application file for complete search history.

(56) References Cited

U.S. PATENT DOCUMENTS

| | | | |
|---|---|---|---|
| 2009/0004413 A1 | 1/2009 | Wagner et al. | |
| 2010/0221521 A1 | 9/2010 | Wagner et al. | |
| 2013/0160638 A1* | 6/2013 | Allison | D01D 5/34 89/36.02 |
| 2015/0344365 A1* | 12/2015 | Keung et al. | C04B 14/062 524/2 |
| 2016/0177156 A1* | 6/2016 | Skrzypski et al. | B01J 13/14 252/74 |

FOREIGN PATENT DOCUMENTS

| | | |
|---|---|---|
| KR | 10-1234525 B1 | 2/2013 |
| WO | 2008-115636 A2 | 9/2008 |
| WO | 2009-053946 A2 | 4/2009 |

OTHER PUBLICATIONS

International Search Report for PCT/KR2013/011629 mailed Aug. 25, 2014 from Korean Intellectual Property Office.

\* cited by examiner

*Primary Examiner* — Nathan M Nutter
(74) *Attorney, Agent, or Firm* — Revolution IP, PLLC

(57) ABSTRACT

Disclosed are a shear thickening fluid (STF) and a polymer composite comprising a core filled with a shear thickening fluid containing silica particles dispersed in polyethylene glycol; an inner capsule layer formed of an emulsifier surrounding the shear thickening fluid; and an outer capsule layer formed of a thermosetting resin surrounding the inner capsule layer.

16 Claims, 2 Drawing Sheets

POLYMER COMPOSITE USING SHEAR THICKENING FLUID

CROSS REFERENCE TO PRIOR APPLICATIONS

This application is a National Stage Application of PCT International Patent Application No. PCT/KR2013/011629 filed on Dec. 16, 2013, under 35 U.S.C. §371, which claims priority to Korean Patent Application No. 10-2013-0135360 filed on Nov. 8, 2013, which are all hereby incorporated by reference in their entirety.

TECHNICAL FIELD

The present invention relates to a polymer complex comprising a shear thickening fluid.

BACKGROUND ART

Suspension or liquid dispersion systems in which fine particles are dispersed in a continuous-phase solvent are divided into the following two categories according to shear rate characteristics: Newtonian fluids that show a constant viscosity regardless of a change in the shear rate; and non-Newtonian fluids whose viscosity changes when the shear rate changes.

A shear thickening fluid (STF), a kind of non-Newtonian fluid, is a fluid such as a colloidal suspension which contains solid particles dispersed in a liquid dispersion medium and which reversibly changes from a liquid state to a solid state due to its rheological properties when the shear stress or shear rate thereof increases to rapidly increase the viscosity.

The shear thickening fluid is usually in a liquid state, and changes to a solid state when a sudden shock is externally applied thereto. Due to this property, studies focused on impregnating the shear thickening fluid into fibers to provide bullet-resistant or stab-resistant materials are currently being actively conducted.

The shear thickening fluid is generally prepared as a sol-type dispersion or suspension by mixing nano-sized silica particles as solid particles with the polar solvent polyethylene glycol as a dispersion medium. In order to bullet-resistant or stab-resistant performance using the shear thickening fluid, it is required to increase the rate of filling of inorganic particles in the shear thickening fluid or the rate of impregnation of the shear thickening fluid in fibers. If the rate of filling of inorganic particles or the rate of impregnation of the shear thickening fluid is increased as described above, there will be a problem in that the impregnated shear thickening fluid flows down to form an agglomerate to thereby greatly reduce rather than increase bullet-resistant performance.

In addition, because the shear thickening fluid is in a liquid state, the use thereof alone may be limited, and the shear thickening fluid will be likely to flow down with the passage of time when it is impregnated into fiber. In addition, when the shear thickening fluid is mixed with a polymer material to prepare a composite, the uniformity of distribution of the shear thickening fluid can decrease. For these reasons, there is a need for studies to solidify the shear thickening fluid so as to widen the range of application thereof and process the shear thickening fluid so as to be uniformly distributed throughout a polymer complex.

DISCLOSURE

Technical Problem

Accordingly, the present invention has been made keeping in mind the above-described problems occurring in the prior art, and an object of the present invention is to provide a capsulate a shear thickening fluid to prepare powder, thereby widening the range of application of the shear thickening fluid and, at the same time, increasing the uniformity of distribution of the shear thickening fluid in a polymer composite to thereby increase the shear thickening ability and elasticity of the shear thickening fluid.

Technical Solution

In order to accomplish the above object, the present invention provides a shear thickening fluid (STF) microcapsule comprising: a core filled with a shear thickening fluid containing silica particles dispersed in polyethylene glycol; an inner capsule layer formed of an emulsifier surrounding the shear thickening fluid; and an outer capsule layer formed of a thermosetting resin surrounding the inner capsule layer.

The emulsifier forming the inner capsule layer of the shear thickening fluid microcapsule may be styrene maleic anhydride.

The thermosetting resin forming the outer capsule layer of the shear thickening fluid microcapsule may be melamine resin, urea resin, phenol resin, a melamine-urea copolymer, a melamine-phenol copolymer, or epoxy resin. Preferably, it may be melamine resin.

In the present invention, the silica particles may be fumed silica particles. The fumed silica particles may have a bimodal particle size distribution in which the size of small-diameter particles is 50-100 nm and the size of large-diameter particles is 110-150 nm. The fumed silica particles may be contained in an amount of 5-30 wt % based on the total weight of the shear thickening fluid.

In the present invention, the silica particles may be spherical silica particles, and the spherical silica particles may be contained in an amount of 20-80 wt % based on the total weight of the shear thickening fluid.

The present invention also provides a method for preparing a shear thickening fluid (STF) microcapsule, comprising the steps of: mixing silica particles and polyethylene glycol at a stirring speed of 120-5000 rpm to prepare a shear thickening fluid (STF); emulsifying the shear thickening fluid by an emulsifier to form an inner capsule layer; adding a polycondensation polymer to the inner capsule layer, and curing the added polycondensation polymer to form an outer capsule layer; and adding a cationic coagulant to the aqueous solution containing the outer capsule layer to solidify the solution, followed by filtration of a solid component.

In the method of the present invention, the emulsifier may be an aqueous solution of styrene maleic anhydride.

The polycondensation polymer is an aqueous solution of melamine formaldehyde.

The step of emulsifying the shear thickening fluid to form the inner capsule layer may comprise performing stirring in an emulsification vessel at a speed of 50,000 rpm or more to form emulsion particles having a particle size of 1-5 μm.

The present invention also provides a polymer composite containing the shear thickening fluid microcapsule. The polymer composite may be selected from among soft polyurethane foam (PUF), a silicon elastomer, and rubber.

Advantageous Effects

The shear thickening fluid microcapsule according to the present invention is prepared by capsulating a conventional liquid shear thickening fluid to prepare powder. Thus, according to the present invention, the range of application of the shear thickening fluid is widened, and the shear thickening fluid is distributed uniformly in a polymer composite so that the shear thickening property and elasticity thereof will be improved.

Mode For Invention

Figure 1:
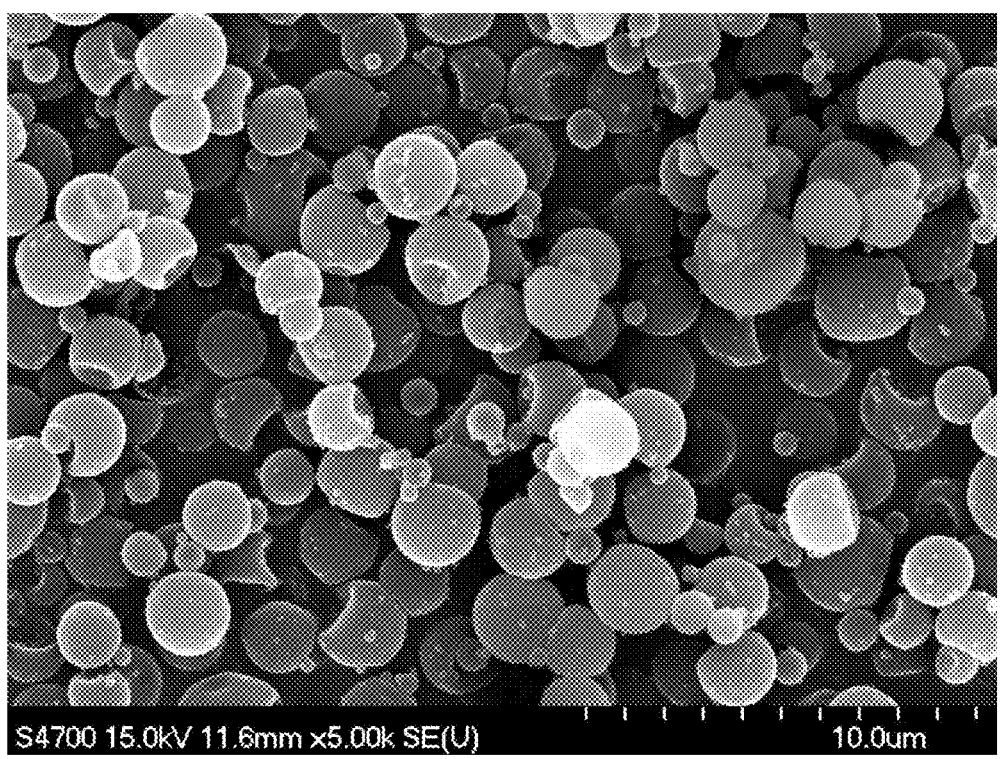
FIG. 1 is an SEM photograph of shear thickening fluid microcapsules containing fumed silica particles, prepared in Example 1 of the present invention.

To achieve the above object, the present inventors have conducted studies to capsule a shear thickening fluid, thereby completing the present invention.

A shear thickening fluid (STF) microcapsule according to the present invention comprises: a core filled with a shear thickening fluid containing silica particles dispersed in polyethylene glycol; an inner capsule layer formed of an emulsifier surrounding the shear thickening fluid; and an outer capsule layer formed of a thermosetting resin surrounding the inner capsule layer.

In the present invention, the silica particles may be any known silica particles such as fumed silica particles or spherical silica particles, which are used in shear thickening fluids. Preferably, the silica particles are fumed silica particles. The fumed silica particles are formed by hydrolysis in flames at a temperature of 1,000° C. or higher as shown in the following reaction equation:

SiCl$_4$+2H$_2$+O$_2$→SiO$_2$+4HCl      Reaction Equation 1

Primary particles made in flames are connected to one another due to mutual collision to form secondary particles which form three-dimensional aggregates (agglomerates). The primary particles of the fumed silica particles are very small in size, are amorphous, and have a large surface area.

Such fumed inorganic particles have advantages over spherical silica particles or colloidal silica particles in that they have a very small primary particle size, are lightweight, have a large surface area, and improve the lightweight properties of products. In addition, such fumed particles have a very big advantage in terms of costs. On the contrary, unlike spherical silica particles in which the size of primary particles is the same as the size of secondary particles, the fumed silica particles have a problem in that they are very difficult to disperse uniformly, due to their aggregation. However, in a previous study, the present inventors found that the fumed silica particles can be effectively controlled to be dispersed and the shear thickening property (bullet-resistant property) thereof is improved, as disclosed in Korean Laid-Open Patent Publication No. 10-2012-0122387.

The fumed silica particles may be distributed non-uniformly and may have a bimodal particle size distribution. This reason is believed to be because the fumed silica particles can be filled at an increased rate while being distributed non-uniformly in a dispersion medium and easily form hydroclusters. This can maximize the frictional force in a thread coming-out phenomenon that occurs upon the collision of a bullet, thereby improving the bullet-resistant property and preventing the fumed silica particles from being separated from bullet-resistant materials.

In the shear thickening fluid comprising the silica particles having a bimodal particle size distribution, the silica particles may have a particle size distribution in which the size of small-diameter silica particles is 50-100 nm and the size of large-diameter silica particles is 110-150 nm. Preferably the silica particles may preferably have a particle size distribution in which the size of small-diameter silica particles is 60-80 nm and the size of large-diameter silica particles is 110-120 nm. Herein, the small-diameter silica particles and the large-diameter silica particles are preferably contained in the shear thickening fluid at a weight ratio of about 6:4 to 9:1, more preferably 7:3. If the silica particles having a particle size difference of about 10-100 nm between the small-diameter silica particles and the large-diameter silica particles as described above are distributed non-uniformly in an organic solvent, preferably in the form of a bimodal particle size distribution, the effect of the non-uniform distribution of the fumed silica particles can be maximized, thereby improving the bullet-resistant property at the same weight and improving the lightweight property.

The silica particles are preferably contained in an amount of 5-30 wt %, more preferably 10-20 wt %, based on the total weight of the shear thickening fluid.

As a dispersion medium for the silica particles, polyethylene glycol which is a polar organic dispersion medium is used. The silica particles are very stably dispersed in the polar dispersion medium, because the silica particles have a large amount of a hydroxyl group on the surface.

The shear thickening fluid of the present invention may be prepared by stirring each component using a mixing device or a homogenizer. Herein, the stirring speed is preferably about 120-3000 rpm for non-uniform particle distribution. If the stirring speed is less than 120 rpm, the solid particles will be difficult to mix with the dispersion medium, and the stirring speed is more than 3000 rpm, it will be difficult to achieve a non-uniform silica particle distribution such as the above-described bimodal particle size distribution.

The spherical silica particles have a high dispersion stability in polyethylene glycol, and thus may be contained in an amount of about 20-80 wt % based on the total weight of the shear thickening fluid.

The prepared shear thickening fluid is emulsified by an emulsifier to form the inner layer of the shear thickening fluid microcapsule.

The emulsifier that is used in the present invention is preferably an aqueous solution of styrene maleic anhydride, but is not limited thereto.

Because styrene maleic anhydride is highly viscous, an aqueous solution containing styrene maleic anhydride at a concentration of 3-8% may be used as the emulsifier.

After the emulsifier is added to the shear thickening fluid, the mixture is introduced in an emulsification vessel and stirred at a speed of 5,000-13,000 rpm to form emulsion particles having a particle size of about 1-5 μm.

After the inner capsule layer is formed of the emulsifier, an excessive amount of melamine resin, urea resin, phenol resin, a melamine-urea copolymer, a melamine-phenol copolymer or an epoxy resin precursor, preferably, a melamine resin precursor, is added to the emulsified solution, and then allowed to react at a temperature of about 80-100° C. for about 8 hours so as to be cured to form an outer capsule layer. A cationic coagulant is added to the prepared microcapsule aqueous solution to solidify the solution, after which the solidified material is filtered, dried and then powdered, thereby obtaining microcapsule powder containing the shear thickening fluid according to the present invention.

Hereinafter, the present invention will be described in detail with reference to preferred examples and comparative examples. The examples of the present invention may, however, be embodied in different forms and should not be construed as limited to the examples set forth herein. Rather, these examples are provided so that this disclosure will be thorough and complete, and will fully convey the scope of the present invention to those skilled in the art.

Materials

Fumed silica particles: Aerosil 200 (A200, Evonik Degussa Corporation) particles were used which are hydrophilic silica particles having a specific surface area (BET) of 200±25 m$^2$/g, an average primary particle size of 12 nm and an equivalent property of about 2.5 [SiOH] group/nm$^2$ or 0.84 mmol/g.

Dispersion medium: polyethylene glycol (molecular weight: 200; Sigma-Aldrich Corporation) was used. It was dried under reduced pressure at 50° C. for 8 hours to remove water.

Example 1

A. 108 g of fumed silica particles were added to 498 g of PEG (molecular weight: 200), and the mixture was stirred using a stirring motor (M8GA6M, Panasonic) and an anchor-type impeller at a speed of 150 rpm for 6 hours, thereby preparing a silica particle dispersion. The prepared silica particle dispersion was allowed to stand at room temperature for 24 hours to remove bubbles, thereby preparing a shear thickening fluid (STF).

B. 150 g of a 5% aqueous solution of styrene maleic anhydride as an emulsifier was added to the prepared shear thickening fluid, and the mixture was introduced into an emulsification vessel and emulsified by stirring at 10,000 rpm for 10 minutes to form an inner capsule layer (emulsion particles: 2-3 μm).

C. An aqueous solution of melamine formaldehyde was added to the emulsified solution (emulsion particles: 2-3 μm) in an amount corresponding to about 20 times the weight of the emulsifier, and then allowed to react at 90° C. for 8 hours, thereby forming an outer capsule layer.

D. A cationic coagulant was added to the resulting aqueous solution, and the obtained solid component was filtered, dried, and then powdered, thereby preparing shear thickening microcapsules.

FIG. 1 is an SEM photograph of the prepared shear thickening fluid microcapsules containing fumed silica particles.

Example 2

Shear thickening fluid microcapsules were prepared in the same manner as described in Example 1, except that 750 g of spherical silica particles were added instead of the fumed silica particles.

Figure 2:
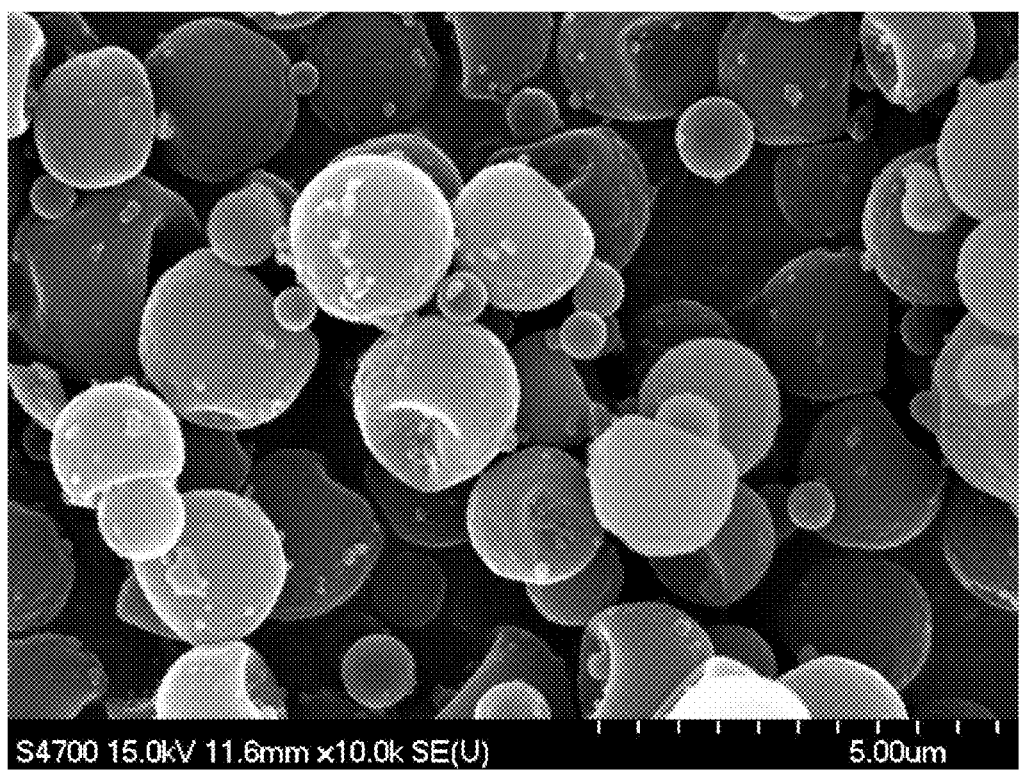
FIG. 2 is an SEM photograph of shear thickening fluid microcapsules containing spherical silica particles, prepared in Example 2 of the present invention.

FIG. 2 is an SEM photograph of the prepared shear thickening fluid microcapsules containing spherical silica particles.

The invention claimed is:

1. A shear thickening fluid (STF) microcapsule comprising:
    a core filled with a shear thickening fluid containing silica particles dispersed in polyethylene glycol;
    an inner capsule layer formed of an emulsifier surrounding the shear thickening fluid; and
    an outer capsule layer formed of a thermosetting resin surrounding the inner capsule layer.

2. The shear thickening fluid microcapsule of claim 1, wherein the emulsifier is styrene maleic anhydride.

3. The shear thickening fluid microcapsule of claim 1, wherein the thermosetting resin is an aqueous solution of melamine formaldehyde which is melamine resin.

4. The shear thickening fluid microcapsule of claim 1, wherein the thermosetting resin is one selected from the group consisting of urea resin, phenol resin, a melamine-urea copolymer, a melamine-phenol copolymer, and epoxy resin.

5. The shear thickening fluid microcapsule of claim 1, wherein the silica particles are fumed silica particles.

6. The shear thickening fluid microcapsule of claim 5, wherein the fumed silica particles have a bimodal particle size distribution.

7. The shear thickening fluid microcapsule of claim 6, wherein the particle size of small-diameter silica particles in the fumed silica particles having the bimodal particle size distribution is 50-100 nm, and the particle size of large-diameter silica particles in the fumed silica particles is 110-150 nm.

8. The shear thickening fluid microcapsule of claim 5, wherein the fumed silica particles are contained in an amount of 5-30 wt % based on the total weight of the shear thickening fluid.

9. The shear thickening fluid microcapsule of claim 1, wherein the silica particles are spherical silica particles.

10. The shear thickening fluid microcapsule of claim 9, wherein the spherical silica particles are contained in an amount of 20-80 wt % based on the total weight of the shear thickening fluid.

11. A method for preparing a shear thickening fluid (STF) microcapsule, comprising the steps of:
    mixing silica particles and polyethylene glycol at a stirring speed of 120-5000 rpm to prepare a shear thickening fluid (STF);
    emulsifying the shear thickening fluid by an emulsifier to form an inner capsule layer;
    adding a polycondensation polymer to the inner capsule layer, and curing the added polycondensation polymer to form an outer capsule layer; and
    adding a cationic coagulant to aqueous solution containing the outer capsule layer to solidify the solution, followed by filtration of a solid component.

12. The method of claim 11, wherein the emulsifier is an aqueous solution of styrene maleic anhydride.

13. The method of claim 11, wherein the polycondensation polymer is an aqueous solution of melamine formaldehyde.

14. The method of claim 11, wherein the step of emulsifying the shear thickening fluid to form the inner capsule layer comprises performing stirring in an emulsification vessel at a speed of 50,000 rpm or more to form emulsion particles having a particle size of 1-5 μm.

15. A polymer composite containing the shear thickening fluid microcapsule of claim 1.

16. The polymer composite of claim 15, wherein the polymer composite is soft polyurethane foam (PUF), a silicon elastomer, or rubber.

* * * * *